United States Patent [19]

Anderson et al.

[11] 4,051,261

[45] Sept. 27, 1977

[54] 1-(P-ALKANOYLPHENYL) ALKANOLS AND DERIVATIVES

[75] Inventors: Paul L. Anderson, Dover; Jeffrey Nadelson, Lake Parsippany, both of N.J.

[73] Assignee: Sandoz, Inc., E. Hanover, N.J.

[21] Appl. No.: 607,779

[22] Filed: Aug. 26, 1975

Related U.S. Application Data

[63] Continuation-in-part of Ser. No. 505,936, Sept. 12, 1974, abandoned, which is a continuation-in-part of Ser. No. 432,832, Jan. 14, 1974, abandoned.

[51] Int. Cl.$^2$ .................. C07C 49/82; A01N 9/24
[52] U.S. Cl. ...................... 424/331; 260/592; 260/591; 260/340.5 R; 260/340.7
[58] Field of Search ................ 260/592; 424/331

[56] References Cited

U.S. PATENT DOCUMENTS

| | | | |
|---|---|---|---|
| 2,438,125 | 3/1948 | Lorand et al. | 260/592 |
| 2,495,904 | 1/1950 | Pines et al. | 260/592 |
| 2,634,294 | 4/1953 | Butler | 260/592 |
| 2,780,649 | 2/1957 | Williams | 260/592 |
| 3,873,539 | 3/1975 | Houlihan et al. | 260/592 |

OTHER PUBLICATIONS

McOmie, Protective Groups in Organic Chemistry, pp. 325-327, (1973).

*Primary Examiner*—James O. Thomas, Jr.
*Assistant Examiner*—James H. Reamer
*Attorney, Agent, or Firm*—Gerald D. Sharkin; Robert S. Honor; Timothy G. Rothwell

[57] ABSTRACT 1-(p-alkanoylphenyl) alkanols, e.g., 1-(p-acetophenyl)-2,2-dimethylpropanol, are prepared from p-alkanoylphenyl Grignard reagents and alkyl and aryl aldehydes or acyl or aroyl halides and are useful as hypolipidemic and anti-diabetic agents.

10 Claims, No Drawings

1-(P-ALKANOYLPHENYL) ALKANOLS AND DERIVATIVES

This application is a continuation-in-part of copending application, Ser. No. 505,936, filed Sept. 12, 1974, now abandoned which in turn is a continuation-in-part of copending application, Ser. No. 432,832, filed Jan. 14, 1974 now abandoned.

This invention relates to 1-(p-alkanoylphenyl) alkanols, their method of preparation, and their use in pharmaceutical compositions. The compounds of this invention may be represented by the following structural formula:

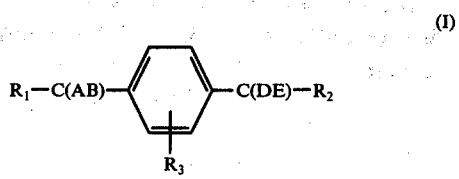
(I)

where $R_1$ is alkyl of 3 to 6 carbons, cycloalkyl having 3 to 6 carbon atoms or

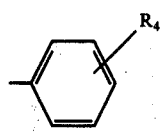

$R_2$ is hydrogen, lower alkyl, i.e., alkyl having 1 to 4 carbon atoms, e.g., methyl, ethyl, isopropyl, and the like, lower alkenyl, i.e., lower alkenyl having 3 to 5 carbon atoms, e.g., allyl, methallyl, and the like, or

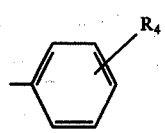

where $R_4$ is hydrogen, halo having an atomic weight of about 19 to 80 or trifluoromethyl, $R_3$ is hydrogen or halo having an atomic weight of about 19 to 80; and —C(AB) and —C(DE)— are > CO, or > CHOH provided that
i. —C(AB)— is different than —C(DE)—;
ii. when $R_1$ is cycloalkyl, —C(AB)— is > CHOH, —C(DE) is > CO and $R_2$ is lower alkyl; and
iii. when $R_1$ is phenyl or substituted phenyl, —C(AB)— is > CHOH.

The preferred compounds of formula (I) are those in which $R_1$ is a tertiary butyl and $R_2$ is methyl. Especially preferred are those compounds in which $R_1$ is tertiary butyl, $R_2$ is methyl and —C(AB)— is > CHOH and those compounds in which $R_1$ is tertiary butyl, $R_2$ is hydrogen and —C(AB)— is —CO—, Compounds of formula (I) tyype in which —C(AB)— is > CHOH and —C(DE)— is

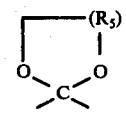

and the compounds of formula (I) type in which —C(AB)— is

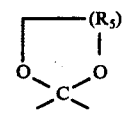

and —C(DE)— is > CO may be prepared according to the following reaction scheme:

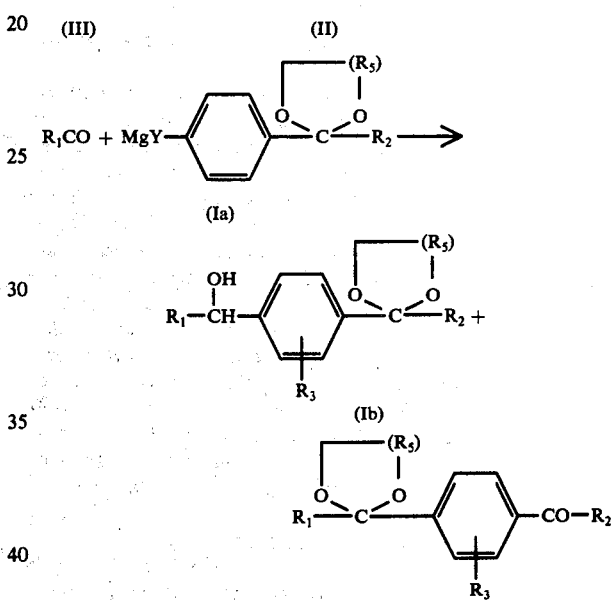

where
Y is halo having an atomic weight of from about 35 to 80, and
$R_5$ is —CH$_2$—, —CH$_2$CH$_2$—or —C(CH$_3$)$_2$CH$_2$— and $R_1$, $R_2$, $R_3$, and the proviso are as set out above.

The compounds of formulae (Ia) and (Ib) are prepared by reacting a Grignard reagent of the formula (II) with a compound of the formula (III) in an inert solvent. It is preferred that the reaction be carried out in an inert solvent such as ethers, e.g., diethyl ether, tetrahydrofuran and the like or aromatic hydrocarbons, e.g., benzene, toluene, xylene and the like, especially tetrahydrofuran. The temperature at which the reaction is carried out is not critical, but it is preferred that the reaction be carried out between about 20° C. to 200°C., preferably between about 30° to 150° C., especially at the reflux temperature of the reaction medium. The time of the reaction also is not critical, but it is preferred that the reaction be run for 1 hour to 24 hours, especially 2 hours to 16 hours. It is also preferred that the reaction be carried out in an inert atmosphere such as argon, helium, or nitrogen, preferably nitrogen. The compounds of formulae (Ia) and (Ib) are isolated by conventional techniques, e.g., evaporation and recrystallization.

The compounds of formula (Ia) may also be prepared according to the following reaction scheme;

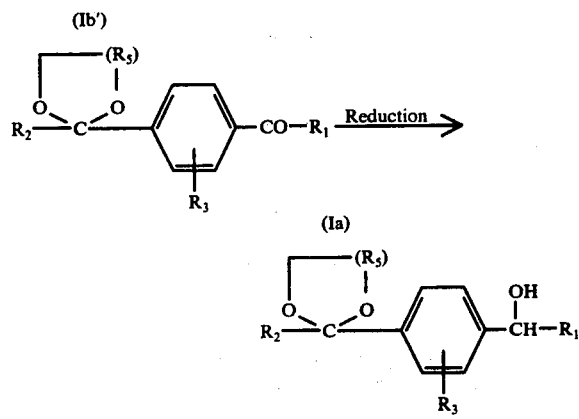

where $R_1$, $R_2$, $R_3$, $R_5$ and the proviso are as set out above.

The compounds of formula (Ia) are prepared by reducing a compound of the formula (Ib') with an organo aluminum hydride, e.g., diisobutyl aluminum hydride, triisobutyl aluminum hydride, sodium bis(2-methoxyethoxy)aluminum hydride, and the like the latter being especially preferred, in the presence of an inert organic solvent. Although the particular solvent used is not critical, it is preferred that the reaction be carried out in the presence of an aromatic hydrocarbon such as benzene, toluene, and the like or an ether such as tetrahydrofuran, diethyl ether, and the like, preferably benzene. The temperature at which the reaction is carried out is not critical, but is is preferred that the reaction be carried out between 0° C. to 30° C., preferably from about 20° C. to 25° C. The reaction may be run from about 30 minutes to 24 hours, preferably from about 30 minutes to 4 hours. The product is recovered using conventional techniques, e.g., chromatography.

The compounds of formula (I) in which C(AB) is hydroxy and —C(DE)— is carbonyl may be prepared according to the following reaction scheme:

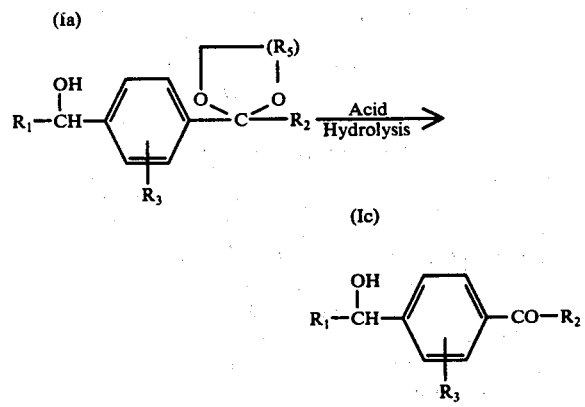

where $R_1$, $R_2$, $R_3$, $R_5$ and the proviso are as defined above.

The compounds of formula (Ic) are prepared by treating a compound of the formula (Ia) with an aqueous inorganic acid. The acid used in the reaction can be any mineral acid, such as sulfuric acid, hydrochloric acid and the like, preferably in dilute form. Although a solvent is not required, it is preferred that the reaction be carried out in an inert solvent such as organic acids, e.g., acetic acid, ethers such as dioxane, tetrahydrofuran, diethyl ether, and the like, especially acetic acid. The temperatures at which the reaction is carried out is not critical, but it is preferred that the reaction be run between 0° C. to 100° C., preferably between about 80° C. to 100° C. The time of the reaction also is not critical, but is preferred that the reaction be run for 1 to 24 hours, especially 1 to 4 hours. The compound of formula (Is) is recovered using conventional techniques, e.g., chromatography.

The compounds of formula (I) in which $R_1$ is tertiary butyl, —C(AB)— is >CO and -C(DE- is >CHOH may be prepared in accordance with the following reaction scheme:

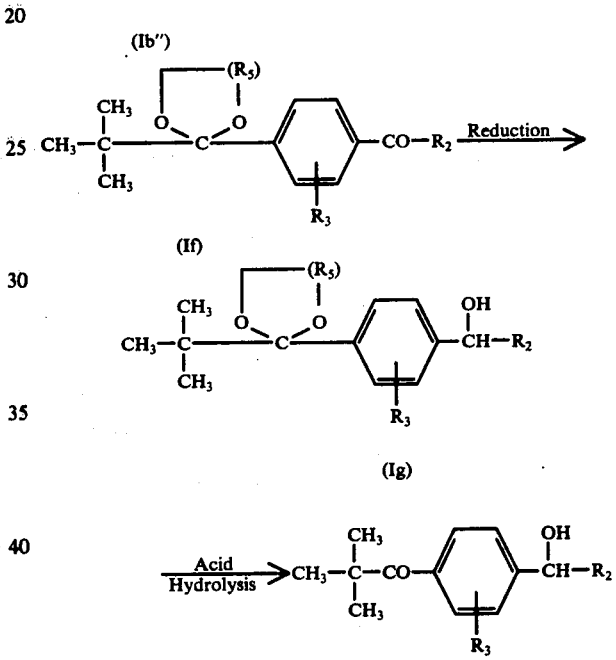

where $R_2$, $R_3$, $R_5$ and the proviso are as set out above.

The compounds of formula (If) are prepared by reducing a compound of the formula Ib") under the same reaction conditions as illustrated above in the reduction of the compounds of formula (Ib'). The compounds of formula (Ig) are prepared by hydrolyzing a compound of the formula (If) with an aqueous acid under the same reaction conditions as employed above in the preparation of the compounds of formula (Ic).

The compounds of formula (Ib) and (Ib') may also be prepared according to the following reaction scheme:

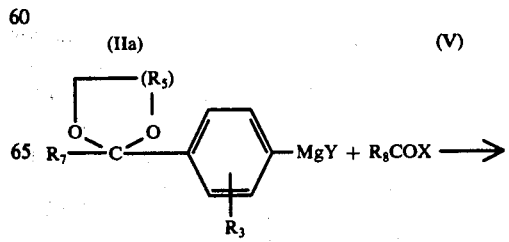

-continued

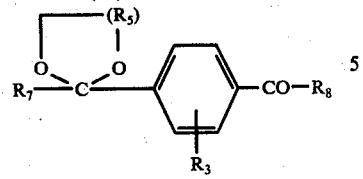

where one of $R_7$ or $R_8$ has the significance of $R_1$ and the other has the significance of $R_2$.

X is halo having an atomic weight of about 35 to 80, and $R_1$, $R_2$, $R_3$, $R_5$, Y and the proviso are as set out above.

The compounds of formula (Ib') are prepared by treating a Grignard reagent of the formula (IIa) with an acid halide of the formula (V) in the presence of an inert organic solvent. Although the particular solvent employed is not critical, the preferred solvents are ethers, such as diethyl ether, dioxane, or tetrahydrofuran, the latter being especially preferred. The temperature of the reaction is not critical, but it is preferred that the reaction be carried out between about 0° C to −80° C., preferably from about −50° C. to −60° C. The reaction may be run from about 1 to 5 hours, preferably from about 2 to 3 hours. The product is recovered using conventional techniques, e.g., evaporation.

The compounds of formula (I) in which $R_1$ is tertiary butyl, —C(AB)— is —CO— and $R_2$ is hydrogen may be prepared by the following reaction scheme:

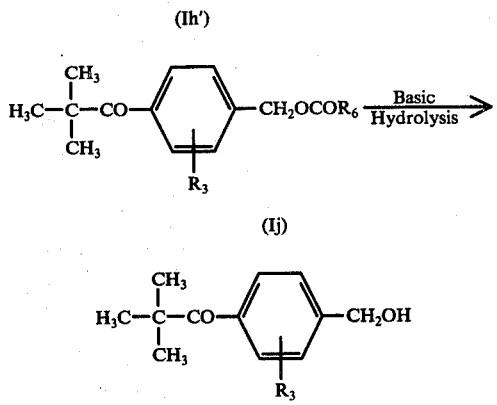

where
$R_6$ is lower alkyl of 1 to 3 carbon atoms and
$R_3$ is as defined above.

The compounds of formula (Ij) are prepared by treating a compound of the formula (Ih') with a base in an aqueous solvent. The base used in the reaction can be any alkali metal base, such as sodium hydroxide, potassium hydroxide, and the like. The aqueous solvent used is not critical, but it is preferred that the reaction be carried out using a water-miscible lower alkanol, such as methanol, ethanol, isopropanol, and the like, especially ethanol. The temperature at which the reaction is carried out also is not critical, but it is preferred that the reaction be run between 40° C. to 150° C., preferably between about 80° C. to 100° C. The time of the reaction also is not critical, but it is preferred that the reaction be run for 1 to 10 hours, for example, about 4 hours. The compound of formula (II) is recovered using conventional techniques, e.g., extraction and evaporation.

The compounds of formula (Ih') are prepared by the following reaction scheme:

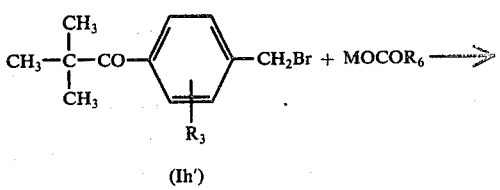

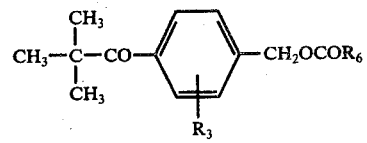

where
M is an alkali metal atom and
$R_3$ and $R_6$ are as defined above.

The compounds of formula (Ih') are prepared by reaction a compound of formula (VI) with a compound of the formula (VII) in an inert solvent. The preferred alkali metals are sodium or potassium and the preferred inert solvents are alcohols of the formula $R_6OH$ where the $R_6$ is the same as in the compound of formula (VII). Potassium acetate is the especially preferred compound of formula (VII) and ethanol is the preferred solvent. The temperature at which the reaction is carried out is not critical, but it is preferred that the reaction be carried out between about 60° C., preferably at the reflux temperature of the reaction medium. The time of the reaction also is not critical, but it is preferred that the reaction be run for about 12 hours to about 30 hours, for example, 20 hours. The compounds of formula (Ih') are recovered by conventional techniques, e.g., extraction and evaporation.

Many of the compounds of formulae (II), (III), (IV), (V), (VI), and (VII) are known and may be prepared by methods described in the literature. Those compounds of formulae (II), (III), (IV), (V), (VI), and (VII) not specifically disclosed may be prepared by analogous methods from known starting materials.

The compounds of formula (I) are useful because they possess pharmacological activity in animals. The compounds of formulae (Ia), (Ib), (Ic), (Id), (Ig), (Ii), and (Ij), in particular, the compounds of formulae (Ia) and (Ib) in which $R_1$ is tertiary butyl, $R_2$ is methyl, and $R_5$ is —CH$_2$—, the compounds of formula (Ic) in which $R_1$ is tertiary butyl and $R_2$ is methyl, the compounds of formula (Ig) in which $R_2$ is methyl and the compound of formula (Ij) are useful as hypolipidemic agents in the treatment of lipidemia, in particular hyperlipoproteinemia, as indicated by the fall in cholesterol and triglyceride levels in male albino Wistar rats weighing 110–130 g. initially. The rats are maintained on drug-free laboratory chow diets for seven days and then divided into groups of 6 to 10 animals. Each group, with the exception of the control, is then given orally 30 to 250 milligrams per kilogram of body weight per diem of the test compound for 6 days. At the end of this period, the animals are anesthetized with sodium hexobarbital and bled from the carotid arteries. Serum or plasma samples are collected and 1.0 ml. of the serum is added to 9.0 ml.

redistilled isopropanol. Two autoanalyzer cupsful of a mixture of zeolite-copper hydroxide and Lloydds reagent (Kersler, G., and Lederer, H., 1965, Technicon Symposium, Madiad Inc., New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

The compounds of formulae (Ia), (Ic), (Ie), and (Ij) in particular, the compounds of formula (Ia) in which $R_5$ is $-CH_2-$, $R_1$ is tertiary butyl, and $R_2$ is ethyl, the compounds of formula (Ic) in which $R_1$ is tertiary butyl and $R_2$ is methyl or hydrogen, and the compound of formula (Ij) are further useful as mature anti-diabetic agents in the treatment of diabetes in adults as indicated by the lowering of blood glucose in 6 to 8 week-old male Royal Hart mice weighing 30 to 35 g., which are fasted in groups of 5 mice for 16 hours and then are given an initial dose of 200 milligrams per kilogram of animal body weight of the compound orally. Two hours after administration, the mice are anesthetized with 85 milligrams per kilogram of animal body weight of sodium hexobarbital after which blood is collected, via cardiac puncture. The blood samples are placed in an Auto Analyzer Cup containing 0.025 milliliters of heparin (1,000 units per milliliter); and the samples are capped, shaken, and stored in ice. The glucose content is determined by the Auto Analyzer potassium ferric-cyanide number N-2b method and are compared with a control group which receive orally 0.5% carboxymethylcellulose vehicle and are run concurrently.

The compounds of formula (Ia), (Ic), (Ig), (Ih), and (Ij) in particular the compounds of fomrula (Ia) in which $R_1$ is tertiary butyl, $R_2$ is ethyl and $R_5$ is $-CH_2-$, the compounds of formula (Ic) in which $R_1$ is tertiaryl butyl and $R_2$ is methyl or hydrogen and the compound of formula (Ih) in which $R_2$ is methyl and $R_6$ is methyl are also useful as juvenile antidiabetic agents in the treatment of diabetes in juveniles as indicated by the lowering of blood glucose in 6 to 8 week old male Royal Hart mice weighing 30 to 35 grams which are fasted in groups of 5 for 16 hours and then are given an initial dose of 200 milligrams per kilogram of animal body weight of the compound orally. One and one half hours later, the mice are given orally 2 grams per kilogram of animal body weight of a glucose challenge. Twenty-five minutes later, the mice are anesthetized with 85 milligrams per kilogram of animal body weight of sodium hexobarbital and 5 minutes later blood is collected via cardiac puncture. The blood samples are placed in an Auto Analyzer Cup containing 0.025 milliliters of heparin (1,000 units per milliliter); and the samples are capped, shaken, and stored in ice. The glucose content is determined by the Auto Analyzer potassium ferric-cyanide N-2b method and are compared with a control group, which receive orally 0.5% carboxymethylcellulose vehicle and are run concurrently.

For such uses, the compounds of formulae (Ia), (Ib), (Ic), (Id), (Ie), (Ig), (Ih), (Ii), and (Ij) may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, and lubricating agents, e.g., magnesiumm stearate, steric acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized by the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The hypolipidemic effective dosage of active ingredient employed for the treatment of lipidemia, in particular, hyperlipoproteinemia and the anti-diabetic effective amount of active ingredient employed in the treatment of diabetes may vary depending on the particular compound employed, the mode of administration and the severity of the condition being treated. However, in general, satisfactory results are obtained for both the hypolipidemic effect and the anti-diabetic effect when the compounds of formula (I) are administered at a daily dosage of from about 2 milligrams to about 250 milligrams per kilogram of animal body weight, p.o., preferably given in divided doses two to four times a day, or in sustained release form. For most large mammals the total daily dosage for both indications is from about 150 to about 2,000 milligrams. Dosage forms suitable for internal use comprise from about 37.5 to about 1,000 milligrams of the active compound in intimate admixture with a solid or liquid pharmaceutically acceptable carrier or diluent.

A representative formulation suitable for oral administration is a tablet or capsule prepared by standard tableting or encapsulating techniques which contains the following and may be administered 2 to 4 times a say in the treatment of lipidemia or diabetes:

| Ingredient | Weight (mg.) tablet | capsule |
|---|---|---|
| 1-(p-acetophenyl)-2,2-dimethyl-propanol | 100 | 100 |
| tragacanth | 10 | — |
| lactose | 247.5 | 300 |
| corn starch | 25 | |
| talcum | 15 | |
| magnesium stearate | 2.5 | |
| TOTAL | 400 mg. | 400 mg. |

The following pharmaceutical compositions are formulated with the indicated amount of active agent using conventional techniques. The injectable suspension and the oral liquid suspension represent formulations useful as unit doses and may be administered in the treatment of lipidemia or diabetes. The injectable suspension is suitable for administration once or twice a day whereas the oral liquid suspension is suitably administered 2 to 4 times per day for this purpose.

| Ingredients | Weight (mg.) sterile injectable suspension | Weight (mg.) oral liquid suspension |
|---|---|---|
| 1-(p-acetophenyl)-2,2-dimethylpropanol | 200 | 100 |
| sodium carboxy methyl-cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | — | 5 |
| sorbitol solution, 70%, U.S.P. | — | 2,500 |
| buffer agent to adjust pH for desired stability | q.s. | q.s. |
| water | for injection, q.s. to 1 ml. | q.s. to 5 ml. |

The preferred pharmaceutical compositions from the standpoint of preparation and ease of administration are solid composition, particularly hard-filled capsules and tablets containing from about 100 to 200 milligrams of the active ingredient.

EXAMPLE 1

1-(p-acetophenyl)-2,2-dimethylpropanol

STEP A

1.

2-methyl-2-(4-[1-hydroxy-2,2-dimethylpropyl]-phenyl)-1,3-dioxolane, and

2.

4-(2,2-dimethyl-1,1-ethylenedioxypropyl)-acetophenone

In 1200 milliliters of toluene in a flask equipped with a Dean-Stark tube are dissolved 100 grams of p-bromoacetophenone and to this solution is added 140 grams of ethylene glycol and 5 grams of p-toluenesulphonic acid. This mixture is refluxed until no further water collects in the Dean-Stark tube. After distilling off 600 milliliters of toluene, the remaining solution is decanted off and evaporated to dryness in vacuo to obtain 2-methyl-2-(p-bromophenyl)-1,3-dioxolane.

In 250 milliliters of tetrahydrofuran, 118 grams of the above dioxolane is dissolved. One quarter of this solution is then added to 12 grams of magnesium, previously washed with chloroform, and refluxed with tetrahydrofuran for 20 minutes; and this mixture is refluxed 4 hours to initiate reaction. Additional dioxolane solution is thereafter added to maintain the refluxing without further heating. After the addition has been completed, 35 grams of 2,2-dimethylpropanol is added and the mixture is refluxed for 2 hours. The reactants are allowed to stand overnight and then poured onto ice-cold ammonium chloride solution. Tetrahydrofuran is added and the two layers formed are allowed to separate. The solvent layer is decanted off and the aqueous layer is extracted twice with 100 milliliters of tetrahydrofuran which are decanted off and combined with the remaining solvent layer. The organic phase is dried over anhydrous magnesium sulphate, filtered and evaporated to dryness to yield a yellow oil which is distilled at 120° to 150° C. and recrystallized from pentane/ether to yield 2-methyl-2-(4-[1-hydroxy-2,2-dimethylpropyl]-phenyl)-1,3-dioxolane (m.p. 75°-80° C).

4-(2,2-dimethyl-1,1-ethylenedioxypropyl)-acetophenone (m.p. 77°-79° C) is obtained as a by product from the above oil and is separated from the main product by column chromatography with benzene as the eluant following which the fraction with an Rf of about 0.6 (chloroform) is fractionally crystallized from pentane.

When the above procedure is carried out using in place of the p-bromoacetophenone of Step A, an equivalent amount of 4-bromo-2-chloro-acetophenone, there is obtained 2-methyl-2-(2-chloro-4[1-hydroxy-2,2-dimethylpropyl]-phenyl)-1,3-dioxolane and 2-chloro-4-(2,2-dimethyl-1,1-ethylenedioxypropyl)-acetophenone.

Following the above reaction, but using in place of the 2,2-dimethylpropanal an equivalent amount of
a. cyclopropyl carboxaldehyde or
b. cyclohexyl carboxaldehyde
there is obtained a. 2-methyl-2-(4-[1-hydroxy-1-cyclopropylmethyl]-phenyl)-1,3-dioxolane (m.p. 58°-61° C) and 4-(1-cyclopropyl-1,1-ethylenedioxymethyl) acetophenone b. 2-methyl-2-(4-[1-hydroxy-1-cyclohexylmethyl]-phenyl)-1,3-dioxolane (m.p. 52°-53° C) and 4-(1-cyclohexyl-1,1-ethylenedioxymethyl) acetophenone (m.p. 37° C); respectively.

When the above process is carried out using an equivalent amount of 2,2-dimethyl-1,3-propanediol in place of the ethylene glycol, there is obtained 2,5,5-trimethyl 2-(4-[1-hydroxy-2,2-dimethylpropyl]-phenyl)-1,3-dioxane (m.p. 117-118 C) and 4-(2,2-dimethyl-1,1-dimethyl-trimethylenedioxypropyl)-acetophenone.

STEP B:

1-(p-acetophenyl)-2,2-dimethylpropanol

The above 2-methyl-2-(4-[1-hydroxy-2,2-dimethylpropyl]-phenyl)-1,3-dioxolane is dissolved in 200 milliliters acetic acid and 65 milliliters of 6N hydrochloric acid are added. The solution is heated on a water bath at about 80°-100° C. for 2 hours and the acetic acid is then removed in vacuo. The residual oil is dissolved in chloroform and washed twice with water after which the chloroform layer is dried over anhydrous magnesium sulphate. The drying agent is filtered off. The chloroform is evaporated off from the filtrate and the oil obtained is recrystallized from pentane ether to obtain 1-(p-acetophenyl)-2,2-dimethylpropanol (m.p. 66°-69° C.). The compound is useful as a hypolipidemic agent and anti-diabetic agent in mammals when administered at a dose of 100 milligrams 2 to 4 times a day.

When the above reaction is carried out using in place of the 2-methyl-2-(4-[1-hydroxy-2,2-dimethylpropyl]-phenyl)-1,3-dioxolane, an equivalent amount of 2-methyl-2-(4-[1-hydroxy-1-cyclohexylmethyl]-phenyl)-1,3-dioxolane, there is obtained 1-cyclohexyl-1-(p-acetophenyl)-carbinol.

EXAMPLE 2

When the process of Example 1 is carried out using an equivalent amount of 2-methylpropanal or heptanal in place of the 2,2-dimethylpropanal, there is obtained after hydrolysis 1-(p-acetophenyl)-2-methylpropanol or 1-(p-acetophenyl)-1-heptanol, respectively.

EXAMPLE 3

4 (1-hydroxyethyl)-2,2-dimethyl propiophenone

STEP A:

4-(2,2-dimethyl-1,1-ethylenedioxypropyl)-α-methylbenzyl alcohol

A solution of 3.0 grams of 4 (2,2-dimethyl-1,1-ethylenedioxypropyl)-acetophenone in 150 ml. tetrahydrofuran is placed in a 250 ml. flask fitted with a dropping funnel and a magnetic stirring bar. Ten milliliters of a 70% solution of sodium bis-(2-methoxyethoxy)-aluminum hydride in benzene is placed in the dropping funnel. The solution is added over 30 minutes, and after the addition is complete, the mixture is stirred for 30 minutes, following which it is poured onto 100 grams of crushed ice to which 50 ml. of saturated ammonium chloride solution has been added. The organic phase is separated and the aqueous phase is extracted thrice with chloroform. The extracts are added to the organic phase, and the combined organic material is dried over anhydrous potassium carbonate. The drying agent is filtered off and the solvent is removed from the filtrate under reduced pressure on a rotary evaporator. The resulting oil is purified by column chromatography using silica gel as the support and benzene as the eluant to give 4-(2,2-dimethyl-1,1-ethylenedioxypropyl)-α-methylbenzyl alcohol, (m.p. 67°-70° C.)

STEP B:

4-(1-hydroxyethyl)-2,2-dimethyl propiophenone 2.6 grams of the above 4-(2,2-dimethyl-1,1-ethylenedioxypropyl)-α-methyl benzyl alcohol is dissolved in a 100 ml. solution of 25% acetic acid containing a small amount of concentrated hydrochloric acid and methanol. The solution is heated on a steam bath for 60 minutes and is then concentrated to one half its volume under reduced pressure distillation. The cooled mixture is extracted with ether twice. The combined ether extracts are washed with water, 10% sodium bicarbonate and then brine. The ether phase is dried over anhydrous magnesium sulfate. The drying agent is filtered off and the solvent is removed from the filtrate under reduced pressure on a rotary evaporator. The residual oil is purified by preparative thin layer chromatography to give an oil 4-(1-hydroxyethyl)-2,2-dimethyl propiophenone.

EXAMPLE 4

2-methyl-2(4-[1-hydroxy-2,2-dimethylpropyl]-phenyl)-1,3-dioxolane

STEP A:

4-(1,1-ethylenedioxyethyl)-pivalophenone

To a suspension of 12.4 g. (0.51 g-atoms) magnesium turnings in 190 ml. tetrahydrofuran under a nitrogen atmosphere, there is added 10 ml. of a solution of 103 g. (0.424 mole) of 4-bromoacetophenone ethylene ketal solution dropwise at a rate that maintains a moderate reflux. After the addition is complete, the mixture is refluxed for one hour. The resulting Grignard solution is added dropwise to a cold solution of 51.1 g. (0.424 mole) pivaloyl chloride in 120 ml. of dry tetrahydrofuran at a rate that maintains the temperature at 0° C. After addition the resulting solution is stirred for 1 hour at −60° C. and then 1 additional hour at −10° C. The mixture is then poured onto ice and extracted with ether, the ether layer is washed with 2N sodium hydroxide, brine, dried over anhydrous magnesium sulfate, filtered and evaporated in vacuo. The resulting residue is triturated with petroleum ether to give 4-(1,1-ethylenedioxyethyl)-pivalophenone (m.p. 75°-82° C.).

When the above procedure is carried out using an equivalent amount of 4-bromopropiophenone ethylene ketal, in place of the 4-bromoacetophenone, there is obtained 4-(1,1-ethylenedioxypropyl)-pivalophenone (m.p. 52°-56° C.).

STEP B:

2-methyl-2-(4-[-hydroxy-2,2-dimethylpropyl]-phenyl-1,3-dioxolane 1.0 gram of 4-(1,1-ethylenedioxyethyl)-pivalophenone is dissolved in 75 ml. of dry tetrahydrofuran in a 150 ml round bottom single-necked flask fitted with a dropping funnel. To the solution there is added dropwise, maintaining the temperature between 20° and 50° C., 10 ml. of a 70% solution of sodium bis(2-methoxyethoxy)-aluminum hydride in benzene. After completing the addition, the mixture is stirred for 30 minutes. A solution of concentrated ammonium chloride is then added cautiously to the cooled reaction. The organic layer is separated and the aqueous phase is extracted with chloroform. The chloroform extract is added to the separated organic layer, and the combined organic phase is dried over anhydrous potassium carbonate. The drying agent is filtered off and the solvent is removed from the filtrate under reduced pressure. The resulting solids are chromatographed on a silica gel column using benzene as an eluant to obtain 2-methyl-2-(4-[1-hydroxy-2,2-dimethylpropyl]-phenyl)-1,3-dioxolane (m.p. 75°-80° C.).

Following the above process and using an equivalent amount of 4-(1,1-ethylenedioxypropyl)-pivalophenone in place of the 4-(1,1-ethylenedioxyethyl)-pivalophenone used therein, there is obtained 2-ethyl-2-(4-[1-hydroxy-2,2-dimethylpropyl]-phenyl)-1,3-dioxolane (m.p. 52°-56° C.).

When the above 2-ethyl-2-(4-[1-hydroxy-2,2-dimethylpropyl]phenyl)-1,3-dioxolane is hydrolyzed in accordance with the procedure of Step B of Example 1, there is obtained 1-(4-propionylphenyl)-2,2-dimethylpropanol (m.p. 88°-91° C.).

EXAMPLE 5

When the process of Example 1 is carried out using an equivalent amount of p-bromopropiophenone or p-bromobenzaldehyde there is obtained following the preparation of 2-ethyl-2-(p-bromophenyl)-1,3-dioxolane, or 2-(p-bromphenyl)-1,3-dioxolane as the major product after carrying out Step A, 2-ethyl-2-(4-[1-hydroxy-2,2-dimethylpropyl]-phenyl)-1,3-dioxolane (m.p. 52°-56° C) or 2-(4-[1-hydroxy-2,2-dimethylpropyl]-phenyl)-1,3-dioxolane and after carrying out Step B, 1-(4-propionylphenyl)-2,2-dimethylpropanol (m.p. 88°-91° C.) or 1-(4-formylphenyl)-2,2-dimethylpropanol (m.p. 42°-46° C.)

EXAMPLE 6

1-(p-benzoylphenyl)-2,2-dimethylpropanol

STEP A:

2-phenyl-2-(4-[1-hydroxy-2,2-dimethylpropyl]-phenyl-1,3-dioxolane

In 1300 milliliters of toluene in a flask equipped with a Dean-Stark tube are dissolved 100 grams of p-bromobenzophenone; and to this solution is added 150 grams of ethyleneglycol and 4.4 grams of p-toluenesulphonic acid. This mixture is refluxed until no further water collects in the Dean-Stark tube. After distilling off the toluene and recrystallization from methanol one obtains 2-phenyl-2-(p-bromophenyl)-1,3-dioxolane.

In 400 milliliters of tetrahydrofuran, 92 grams of the above dioxolane is dissolved. One quarter of this solution is then added to 7.4 grams of magnesium, previously washed with chloroform and refluxed with tetrahydrofuran for 20 minutes; and this mixture is refluxed for 1 hour. Additional dioxalane solution is thereafter added to maintain the refluxing without further heating. After the addition has been completed, 26 grams of 2,2-dimethylpropanal dissolved in 150 ml. of tetrahydrofuran is added and the mixture is stirred for 15 hours at room temperature. The mixture is then poured onto ice-cold ammonium chloride solution. Tetrahydrofuran is added and the two layers formed are allowed to separate. The solvent layer is decanted off and the aqueous layer is extracted thruce more with 100 milliliters of ether which are decanted off and combined with the remaining solvent layer. The organic phase is dried over magnesium sulphate, filtered and evaporated to dryness to yield a crude product which is chromatographed and the product recrystallized from pentane/ether to yield 2-phenyl-2-(4-[1-hydroxy-2,2-dimethylpropyl]-phenyl)-1,3-dioxolane (m.p. 90°-93° C.).

Following the above reaction but using an equivalent amount of
a. 4-chloro-4-bromo-benzophenone or
b. 3-trifluoromethyl-4-bromo-benzophenone in place of the p-bromoacetophenone, there is obtained
a. 2-(p-chlorophenyl)-2-(4-[2-hydroxy-2,2-dimethylpropyl]-phenyl)-1,3-dioxolane,
b. 2-(p-trifluoromethylphenyl)-2-(4-[2-hydroxy-2,2-dimethyl-propyl]-phenyl)-1,3-dioxolane, respectively.

STEP B: 1-p-benzoylphenyl-2,2-dimethylpropanol 14.2 gr. of the above 2-phenyl-2-(4-[1-hydroxy-2,2-dimethylpropyl]-phenyl)-1,3-dioxolane is dissolved in 500 milliliters 25% acetic acid and 5 milliliters of concentrated hydrochloric acid are added. The solution is heated on a water bath at about 60° C. for two hours. The mixture is then treated with 300 ml. of saturated sodium chloride and extracted three times with ether. The combined ether layers are washed with saturated sodium chloride solution, 2N sodium hydroxide and then dried over anhydrous magnesium sulfate and filtered. The solvent is removed and the solid recrystallized from ether-petroleum ether to give 1-(p-benzoylphenyl)-2,2-dimethylpropanol (m.p. 103°-105° C.).

When the above reaction is carried out using in place of the 2-phenyl-2-(4-[1-hydroxy-2,2-dimethylpropyl]-phenyl)-1,3-dioxolane, an equivalent amount of
a. 2-(p-chlorophenyl)-2-(4-[2-hydroxy-2,2-dimethylpropyl]-phenyl)-1,3-dioxolane,
b. 2-(m-trifluoromethylphenyl)-2-(4-[2-hydroxy-2,2-dimethylphenyl]-phenyl)-1,3-dioxolane or
c. 2-allyl-2-(4-[2-hydroxy-2,2-dimethylphenyl]-phenyl)-1,3-dioxolane, there is obtained
a. 1-(p-chlorobenzoylphenyl)-2,2-dimethylpropanol,
b. 1-(m-trifloromethylbenzoylphenyl)-2,2-dimethylpropanol or
c. 1-(p-allylphenyl)-2,2-dimethylpropanol, respectively.

EXAMPLE 7

When the process of Example 1 is carried out using an equivalent amount of 3-trifluoromethyl-benzaldehyde in place of 2,2-dimethylpropanal, there is obtained following the preparation of 2-methyl-2-(p-bromophenyl)-1,3-dioxolane, as the major product after carrying out Step A, 2-methyl-2-(4-[(3-trifluoromethyl)-α-hydroxybnzyl]phenyl)-1,3-dioxolane; and after carrying out Step B., 3-trifluoromethylphenyl-4-acetophenyl-carbinol. (m.p. 60° to 63° C.)

EXAMPLE 8 p-pivaloyl-benzyl alcohol

Step 1--α-acetoxy-p-pivaloyl-toluene

A mixture of 20.0 grams (0.0785 mole) of α-bromo-p-pivaloyl toluene, 30.0 grams (0.157 mole) of potassium acetate and 60 milliliters of glacial acetic acid is refluxed for 20 hours. The acetic acid is removed in vacuo, and the residue is treated with ice water and then extracted with methylene chloride. The methylene chloride extract is washed with 2N sodium hydroxide solution, dried with magnesium suflate, and then filtered and evaporated to give α-acetoxy-p-pivaloyl toluene.

Following the above procedure, but using α-bromo-2-chloro-4-pivaloyl-toluene in place of the α-bromo-p-pivaloyl toluene there is obtained α-acetoxy-2-chloro-4-pivaloyl-toluene.

Step 2--p-pivaloyl-benzyl alcohol

A mixture of 15 grams (0.064 mole) of α-acetoxy-p-pivaloyl toluene and 15 grams (0.278 mole) of potassium hydroxide in 150 milliliters of ethanol and 50 milliliters of water is refluxed for four hours. The solvent is removed in vacuo, and the residue is treated with ether and water. The ether is separated and the water is again extracted with ether. The ether layers are combined, decolorized with charcoal, dried over magnesium sulfate, filtered and evaporated. The resulting yellow oil is distilled in vacuo to give p-pivaloyl benzyl alcohol (b.p. 100°-105° C./0.1 mm).

Following the above procedure, but using an equivalent amount of α-acetoxy-2-chloro-4-pivaloyl-toluene in plce of the α-acetoxy-p-pivaloyl-toluene, there is obtained 2-chloro-4-pivaloyl-benzyl alcohol.

The p-pivaloyl-benzyl alcohol of this Example is especially effective as an anti-diabetic agent when administered at a daily dosage of from about 10 milligrams to about 200 milligrams per kilogram of animal body weight, p.o., preferably given in divided doses two to four times a day, or in sustained release form. For most large mammals, the preferred total daily dosage is from about 750 to about 3,000 milligrams. Dosage forms suitable for internal use comprise from about 185.5 to 1500 milligrams of the active compound in intimate admixture with a solid or liquid pharmaceutically acceptable carrier or diluent.

What is claimed is:

1. A compound of the formula

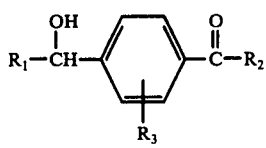

where

R₁ is t-butyl or cycloalkyl having 3 to 6 carbon atoms, and

R₂ is lower alkyl having 1 to 4 carbon atoms or lower alkenyl having 3 to 5 carbon atoms, and R₃ is hydrogen or halo having an aomic weight of about 19 to 80, provided that when R₁ is cycloalkyl, R₂ is lower alkyl.

2. A compound of the formula

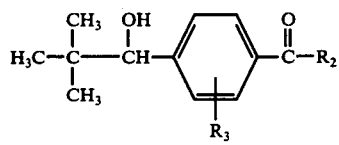

where

R₂ is lower alkyl having 1 to 4 carbon atoms or lower alkenyl having 3 to 5 carbon atoms, and R₃ is hydrogen or halo having an atomic weight of about 19 to 80.

3. A compound of claim 1, in which R₁ is tertiary butyl and R₂ is methyl.

4. The compound of claim 1, which is 1-(p-acetophenyl)-2,2-dimethylpropanol.

5. The compound of claim 1, which is 1-cyclohexyl-1-(p-acetophenyl)-carbinol.

6. The compound of claim 1, which is 1-(4-propionylphenyl)-2,2-dimethylpropanol.

7. A pharmaceutical composition comprising as the active ingredient a therapeutically effective amount of a compound according to claim 1 in combination with a pharmaceutically acceptable carrier or excipient.

8. A method of treating lipidemia, which comprises administering to a mammal in need of said treatment a therapeutically effective amount of a compound according to claim 1.

9. A method of treating diabetes in adult mammals, which comprises administering to a mammal in need of said treatment a therapeutically effective amount of a compound according to claim 1.

10. A method of treating diabetes in juvenile mammals, which comprises administering to a mammal in need of said treatment a therapeutically effective amount of a compound according to claim 1.

* * * * *